(12) United States Patent
Koike et al.

(10) Patent No.: US 9,193,805 B2
(45) Date of Patent: Nov. 24, 2015

(54) DEXTRIN FATTY ACID ESTER THAT DOES NOT CAUSE GELATION OF LIQUID OIL, AND USES THEREOF

(75) Inventors: Hideaki Koike, Chiba (JP); Takanao Suzuki, Chiba (JP); Daisuke Tsukioka, Chiba (JP); Satsuki Miyagawa, Tokyo (JP); Yuriko Tomita, Tokyo (JP); Keiji Igarashi, Tokyo (JP)

(73) Assignees: Chiba Flour Milling Co., Ltd., Chiba (JP); KOSE Corporation, Tokyo (JP)

( * ) Notice: Subject to any disclaimer, the term of this patent is extended or adjusted under 35 U.S.C. 154(b) by 154 days.

(21) Appl. No.: 13/578,412

(22) PCT Filed: Feb. 16, 2011

(86) PCT No.: PCT/JP2011/000848
§ 371 (c)(1),
(2), (4) Date: Aug. 10, 2012

(87) PCT Pub. No.: WO2011/102123
PCT Pub. Date: Aug. 25, 2011

(65) Prior Publication Data
US 2012/0316332 A1    Dec. 13, 2012

(30) Foreign Application Priority Data

Feb. 19, 2010   (JP) .................................. 2010-034746
Mar. 25, 2010   (JP) .................................. 2010-071129
Mar. 30, 2010   (JP) .................................. 2010-079414

(51) Int. Cl.
| | | |
|---|---|---|
| C08B 31/04 | (2006.01) | |
| C09D 103/06 | (2006.01) | |
| A61K 8/73 | (2006.01) | |
| A61Q 19/00 | (2006.01) | |
| C07H 13/06 | (2006.01) | |
| C08B 30/18 | (2006.01) | |
| C09D 7/02 | (2006.01) | |
| C09D 11/14 | (2006.01) | |
| C11C 3/00 | (2006.01) | |

(52) U.S. Cl.
CPC . *C08B 31/04* (2013.01); *A61K 8/73* (2013.01); *A61Q 19/00* (2013.01); *C07H 13/06* (2013.01); *C08B 30/18* (2013.01); *C09D 7/02* (2013.01); *C09D 11/14* (2013.01); *C11C 3/00* (2013.01); *A61K 2800/10* (2013.01)

(58) Field of Classification Search
CPC ....... C08B 31/04; C09D 103/06; A61K 8/732
See application file for complete search history.

(56) References Cited

U.S. PATENT DOCUMENTS

| | | | |
|---|---|---|---|
| 1,959,590 A | | 5/1934 | Lorand |
| 4,780,145 A | | 10/1988 | Mori et al. |
| 5,106,625 A | * | 4/1992 | Yamamoto et al. ........... 424/401 |
| 5,840,883 A | * | 11/1998 | Suzuki et al. ................. 536/103 |

FOREIGN PATENT DOCUMENTS

| | | |
|---|---|---|
| EP | 1992324 A1 | 4/2008 |
| GB | 1185943 A | 3/1970 |
| JP | 63-033311 | 2/1988 |
| JP | 08-277302 | 10/1996 |
| JP | 10-025362 | 1/1998 |
| JP | 2001-039817 | 2/2001 |
| JP | 2002-193740 | 7/2002 |
| JP | 2002-255727 | 11/2002 |
| JP | 2002-363030 | 12/2002 |
| JP | 2002370928 A | 12/2002 |
| JP | 2003095847 A | 4/2003 |
| JP | 2003119107 A | 4/2003 |
| JP | 2004-359682 | 12/2004 |
| JP | 2005145851 A | 6/2005 |
| JP | 2006-169143 | 6/2006 |
| JP | 2008106049 A | 5/2008 |
| WO | 02/03939 A2 | 1/2002 |

OTHER PUBLICATIONS

Extended European Search Report, EP 11 74 4414, dated Oct. 29, 2013.
International Search Report PCT/JP2011/000848 dated Sep. 27, 2012.

* cited by examiner

*Primary Examiner* — Jonathan S Lau

(57) ABSTRACT

An object of the present invention is to provide novel dextrin fatty acid ester that is excellent in tackiness and useful as a base for cosmetics and the like. The novel dextrin fatty acid ester is prepared by esterification between dextrin and fatty acids, wherein the dextrin has an average degree of glucose polymerization of 3 to 150; the fatty acids comprise more than 50 mol % and 100 mol % or less, based on the total amount of the fatty acids, of one or more saturated branched fatty acids having 4 to 26 carbon atoms, and 0 mol % or more and less than 50 mol %, based on the total amount of the fatty acids, of one or more fatty acids selected from the group consisting of saturated linear fatty acids having 2 to 22 carbon atoms, unsaturated linear or branched fatty acids having 6 to 30 carbon atoms, and saturated or unsaturated cyclic fatty acids having 6 to 30 carbon atoms; and the degree of substitution by the fatty acids is 1.0 to 3.0 per glucose unit.

4 Claims, 1 Drawing Sheet

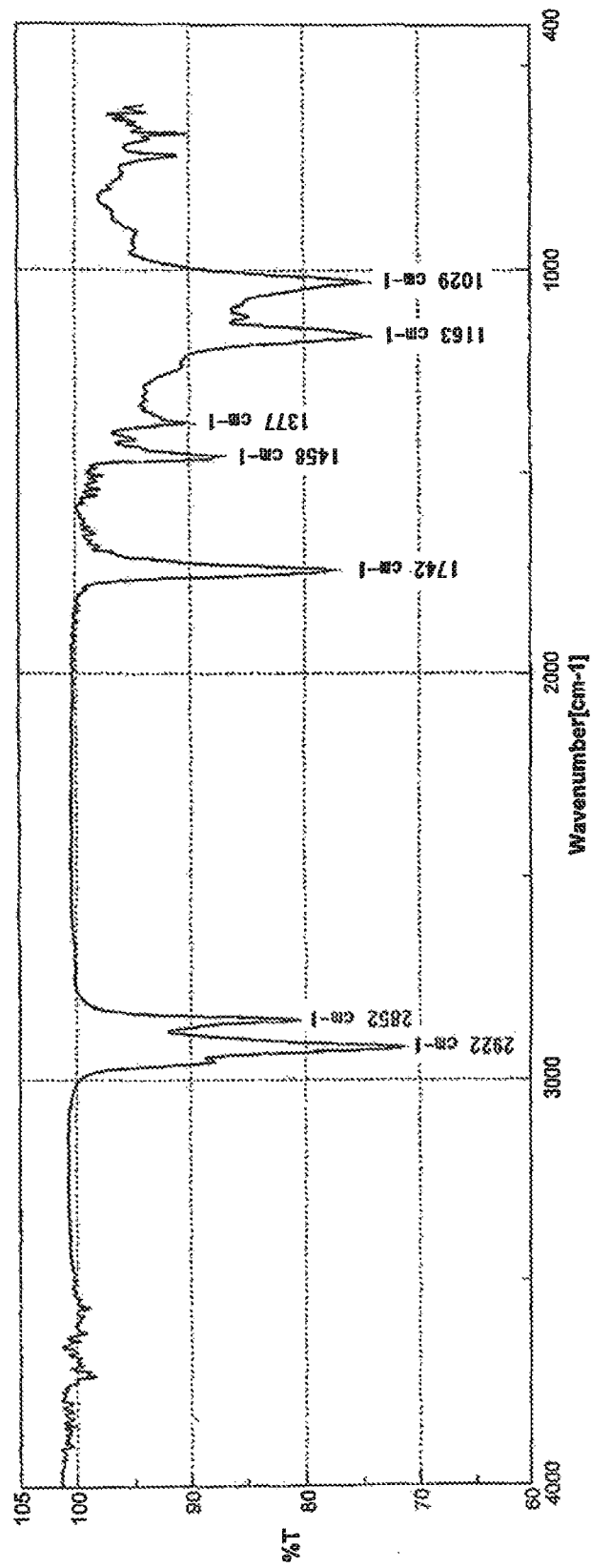

DEXTRIN FATTY ACID ESTER THAT DOES NOT CAUSE GELATION OF LIQUID OIL, AND USES THEREOF

TECHNICAL FIELD

The present invention relates to novel dextrin fatty acid ester prepared by esterification between dextrin and particular fatty acids, and uses thereof. Particularly, the present invention relates to novel dextrin fatty acid ester that does not cause gelation of liquid oil.

BACKGROUND ART

Various types of resins have been used in cosmetics. A large number of products have been developed by using shape-retaining ability brought about by the adhesion (tackiness) and hardness of these resins. Resins are broadly classified into: naturally-derived resins whose starting materials are natural plant-derived resins, for example, pine resin, dammar, mastic, copal, amber, balsam, and Japanese lacquer or natural animal-derived resins, for example, shellac; and synthetic resins synthesized from chemicals with petroleum as a material. Particularly, the natural plant-derived resins are used in not only cosmetics but also in foods such as chewing gum. For example, rosin acid pentaerythritol ester is a naturally-derived resin prepared by esterification between abietic acid contained in a solid resin called rosin (obtained from the secretory fluid of pine) and pentaerythritol (natural sugar alcohol) (see patent document 1), and is also currently used in general in cosmetics and foods. Unfortunately, this resin, in cosmetics, often presents an odor problem, which tends to be made more noticeable by heating for dissolution. In addition, its film has a little adhesion and thus requires adding a plasticizer for adjustment. In some cases, the resin contained therein in large amounts may impair the texture of the cosmetic.

Alternatively, for example, a silicone resin has been used as a synthetic resin (see patent document 2). Although this resin is free from problems associated with safety, odor, or texture, it may be difficult, particularly, for cosmetics, to impart the affinity of the film for the skin due to its poor adhesion to the skin.

Thus, attention has been focused on naturally-derived dextrin fatty acid ester. However, some conventional dextrin fatty acid esters (patent document 3), which are prepared by esterification of branched fatty acids, cause gelation of liquid oil, but have insufficient adhesion (tackiness).

PRIOR ART DOCUMENTS

Patent Documents

Patent Document 1: Japanese Patent No. 3575510
Patent Document 2: Japanese Patent Publication No. 48-1503
Patent Document 3: Japanese Patent No. 3019191

SUMMARY OF THE INVENTION

Object to be Solved by the Invention

Thus, an object of the present invention is to provide a material that can overcome various disadvantages of the conventional techniques described above, particularly, novel dextrin fatty acid ester excellent in tackiness.

Means to Solve the Object

The present inventors have found that dextrin fatty acid ester prepared by esterification between dextrin and a mixture of saturated branched fatty acids with saturated linear fatty acids, unsaturated fatty acids, and/or saturated or unsaturated cyclic fatty acids at particular ratios, or saturated branched fatty acids alone does not cause gelation of liquid oil and is excellent in tackiness, and have also found that this dextrin fatty acid ester can be used in cosmetics and the like. Based on these findings, the present invention has been completed.

Specifically, the present invention relates to:
(1) a dextrin fatty acid ester prepared by esterification between dextrin and fatty acids, wherein the dextrin has an average degree of glucose polymerization of 3 to 150; the fatty acids comprise more than 50 mol % and 100 mol % or less, based on the total amount of the fatty acids, of one or more saturated branched fatty acids having 4 to 26 carbon atoms, and 0 mol % or more and less than 50 mol %, based on the total amount of the fatty acids, of one or more fatty acids selected from the group consisting of a saturated linear fatty acid having 2 to 22 carbon atoms, an unsaturated linear or branched fatty acid having 6 to carbon atoms, and a saturated or unsaturated cyclic fatty acid having 6 to 30 carbon atoms; and the degree of substitution by the fatty acids is 1.0 to 3.0 per glucose unit;
(2) the dextrin fatty acid ester according to (1), wherein the saturated branched fatty acid is one or more saturated branched fatty acids having 12 to 22 carbon atoms;
(3) the dextrin fatty acid ester according to (1) or (2), wherein the dextrin fatty acid ester is not capable of causing gelation of liquid paraffin having a kinematic viscosity at 40° C. of 8 $mm^2$/s as measured by ASTM D445 test method; and
(4) the dextrin fatty acid ester according to any one of (1) to (3), wherein change in load (maximum stress value) applied to the point of contact is 30 to 1000 g when 100 g of load is applied to a film using a texture analyzer, kept for 10 seconds, and then separated therefrom at a rate of 0.5 mm/second, wherein the film has been obtained by applying a light liquid isoparaffin solution containing 40% by mass of the dextrin fatty acid ester at a thickness of 400 μm on a glass plate using an applicator, followed by drying.

The present invention also relates to:
(5) a method for producing a dextrin fatty acid ester, comprising reacting dextrin having an average degree of glucose polymerization of 3 to 150 with a fatty acid derivative comprising more than 50 mol % and 100 mol % or less, based on the total amount of the fatty acid derivatives, of one or more saturated branched fatty acid derivatives having 4 to 26 carbon atoms and 0 mol % or more and less than 50 mol %, based on the total amount of the fatty acid derivatives, of one or more fatty acid derivatives selected from the group consisting of a saturated linear fatty acid derivative having 2 to 22 carbon atoms, an unsaturated linear or branched fatty acid derivatives having 6 to 30 carbon atoms, and saturated or unsaturated cyclic fatty acid derivatives having 6 to 30 carbon atoms; and
(6) a method for producing a dextrin fatty acid ester, comprising reacting dextrin having an average degree of glucose polymerization of 3 to 150 with one or more saturated branched fatty acid derivatives having 4 to 26 carbon atoms and subsequently reacting the product with one or more fatty acid derivatives selected from the group consisting of a saturated linear fatty acid derivative having 2 to 22 carbon atoms, an unsaturated linear or branched fatty acid derivative having 6 to 30 carbon atoms, and a saturated or unsaturated cyclic fatty acid derivatives having 6 to 30 carbon atoms, wherein the one or more saturated branched fatty acid derivatives having 4 to 26 carbon atoms are used in an amount of more than 50 mol % and 100 mol % or less based on the total amount of the fatty acid derivatives, and the one or more fatty acid derivatives selected from the group consisting of a saturated linear fatty acid derivative having 2 to 22 carbon atoms, an unsaturated linear or branched fatty acid derivatives having 6 to 30 carbon atoms, and a saturated or unsaturated cyclic fatty acid derivative having 6 to 30 carbon atoms are used in an amount of 0 mol % or more and less than 50 mol % based on the total amount of the fatty acid derivatives.

The present invention further relates to:
(7) a base for a cosmetic, a pharmaceutical drug, a quasi-drug, stationery, paint, or ink, containing the dextrin fatty acid ester according to any one of (1) to (4); and
(8) a base for a cosmetic, a pharmaceutical drug, a quasi-drug, stationery, paint, or ink, containing a dextrin fatty acid ester obtained by the production method according to (5) or (6).

BRIEF DESCRIPTION OF DRAWINGS

FIG. 1 is a diagram showing the IR chart of dextrin fatty acid ester of Production Example 1.

MODE OF CARRYING OUT THE INVENTION

The present invention will be described in more detail.
(Dextrin Fatty Acid Ester)

Dextrin fatty acid ester of the present invention is prepared by esterification between dextrin and fatty acids. The degree of substitution of the dextrin by the fatty acids is 1.0 to 3.0, preferably 1.2 to 2.8, per glucose unit. This degree of substitution less than 1.0 is not preferable because the resulting dextrin fatty acid ester requires a temperature as high as 100° C. or higher for its dissolution in liquid oil or the like and produces stains or unusual odors.

The dextrin fatty acid ester of the present invention has the following properties:
1) The dextrin fatty acid ester of the present invention does not cause gelation of liquid oil when mixed with the liquid oil.

The phrase "not cause gelation of liquid oil" means that, when liquid paraffin having a kinematic viscosity at 40° C. of 8 mm$^2$/s as measured by ASTM D445 test method is used as the liquid oil, the liquid paraffin containing 5% by mass of the dextrin fatty acid ester of the present invention is dissolved at 100° C. and measured 24 hours later to have a viscosity equal to or lower than the detection limit in viscosity measurement at 25° C. using Yamco DIGITAL VISCOMATE viscometer VM-100A (oscillatory) (manufactured by Yamaichi Electronics Co., Ltd.). It can be confirmed that viscosity is detected if the gelation of the liquid oil is caused.
2) A film formed from the dextrin fatty acid ester of the present invention has tackiness in a particular range.

The "tackiness" may be indicated by change in load (maximum stress value) applied to the point of contact from the start of retrograde movement to complete separation when the dextrin fatty acid ester is applied to a support, with which another support is surface-contacted from a position some distance therefrom and then separated therefrom by the retrograde movement. Thus, the change in load, i.e., the tackiness, is 30 to 1000 g when 100 g of load is applied to a film using a texture analyzer, for example, Texture Analyzer TA.XTplus (manufactured by Stable Micro Systems Ltd.) and a probe made of a cylindrical polyacetal resin of 12.5 mm in diameter (Delrin (registered trademark) manufactured by DuPont), kept for 10 seconds, and then separated therefrom at a rate of 0.5 mm/second, wherein the film has been obtained by applying a light liquid isoparaffin solution containing 40% by mass of the dextrin fatty acid ester at a thickness of 400 μm on a glass plate using an applicator, followed by drying.

The dextrin used in the dextrin fatty acid ester of the present invention is preferably dextrin having an average degree of glucose polymerization of 3 to 150, particularly, 10 to 100. If the average degree of glucose polymerization is 2 or less, the resulting dextrin ester is in a wax-like form having reduced solubility in an oil solution. Alternatively, if the average degree of glucose polymerization exceeds 150, the resulting dextrin ester, for example, may disadvantageously require a higher temperature for its dissolution in an oil solution or have poor solubility. The dextrin may have any of linear, branched, and cyclic sugar chains.

The fatty acids used in the dextrin fatty acid ester of the present invention inevitably comprise one or more saturated branched fatty acids having 4 to 26 carbon atoms and may further comprise one or more fatty acids selected from the group consisting of saturated linear fatty acids having 2 to 22 carbon atoms, unsaturated linear or branched fatty acids having 6 to 30 carbon atoms, and saturated or unsaturated cyclic fatty acids having 6 to 30 carbon atoms (hereinafter, these fatty acids other than the saturated branched fatty acids having 4 to 26 carbon atoms are also collectively referred to as "the other fatty acids").

The compositional ratios of the fatty acids in the present invention are more than 50 mol % and 100 mol % or less, preferably 55 mol % or more and 100 mol % or less, based on the total amount of the fatty acids, of one or more saturated branched fatty acids having 4 to 26 carbon atoms and 0 mol % or more and less than 50 mol %, preferably 0 mol % or more and 45 mol % or less, based on the total amount of the fatty acids, of the other fatty acids.

Examples of the saturated branched fatty acids having 4 to 26 carbon atoms, used in the present invention, include isobutyric acid, isovaleric acid, 2-ethylbutyric acid, ethylmethylacetic acid, isoheptanoic acid, 2-ethylhexanoic acid, isononanoic acid, isodecanoic acid, isotridecanoic acid, isomyristic acid, isopalmitic acid, isostearic acid, isoarachic acid, and isohexacosanoic acid. One or more of these fatty acids can be selected or combined appropriately for use. Of them, fatty acids having 12 to 22 carbon atoms are preferable, and isostearic acid is particularly preferable, with no limitation imposed on structural difference, etc.

In the present invention, the isostearic acid means one branched stearic acid or a mixture of two or more branched stearic acids. For example, 5,7,7-trimethyl-2-(1,3,3-trimethylbutyl)-octanoic acid can be produced by converting an isobutylene dimer to branched aldehyde having 9 carbon atoms through oxo reaction and subsequently this aldehyde to unsaturated branched aldehyde having 18 carbon atoms through aldol condensation, followed by hydrogenation and oxidation (hereinafter, abbreviated to "aldol condensation type"). This is commercially available from, for example, Nissan Chemical Industries, Ltd. 2-heptylundecanoic acid can be produced by Guerbet reaction with nonyl alcohol, followed by oxidation. This is commercially available from, for example, Mitsubishi Kasei Corp. An analogous mixture slightly differing in branch position therefrom is commercially available from Nissan Chemical Industries, Ltd. In addition, a type that is produced from a starting alcohol other than a saturated linear alcohol and methyl-branched at two positions is also commercially available from Nissan Chemical Industries, Ltd. (hereinafter, collectively abbreviated to "Guerbet reaction type"). Furthermore, methyl-branched isostearic acid is obtained as a by-product during, for example, oleic acid dimer production [described in, e.g., J. Amer. Oil Chem. Soc., 51, 522 (1974)] and is commercially available from, for example, Emery Industries, Inc., USA (hereinafter, abbreviated to "Emery type"). A starting material for dimer acid serving as a starting material for Emery-type isostearic acid may comprise not only oleic acid but also linoleic acid, linolenic acid, and the like. In the present invention, this Emery type is particularly preferable.

Examples of the saturated linear fatty acids having 2 to 22 carbon atoms, used in the present invention, include acetic acid, caprylic acid, capric acid, lauric acid, myristic acid, palmitic acid, stearic acid, arachic acid, and behenic acid. One or more of these fatty acids can be selected or combined appropriately for use. Of them, fatty acids having 8 to 22 carbon atoms are preferable, and fatty acids having 12 to 22 carbon atoms are particularly preferable.

Examples of the unsaturated linear or branched fatty acids having 6 to 30 carbon atoms, used in the present invention, include: unsaturated monoenoic fatty acids such as cis-4-decenoic (obtusilic) acid, 9-decenoic (caproleic) acid, cis-4-dodecenoic (linderic) acid, cis-4-tetradecenoic (tsuzuic) acid, cis-5-tetradecenoic (physeteric) acid, cis-9-tetradecenoic (myristoleic) acid, cis-6-hexadecenoic acid, cis-9-hexadecenoic (palmitoleic) acid, cis-9-octadecenoic (oleic) acid, trans-9-octadecenoic acid (elaidic acid), cis-11-octadecenoic (asclepinic) acid, cis-11-eicosenoic (gondoic) acid, cis-17-hexacosenoic (ximenic) acid, and cis-21-triacontenoic (lumequeic) acid; and unsaturated polyenoic fatty acids such as sorbic acid, linoleic acid, hiragonic acid, punica acid, linolenic acid, γ-linolenic acid, moroctic acid, stearidonic acid, arachidonic acid, EPA, clupanodonic acid, DHA, nisinic acid, stearolic acid, crepenynic acid, and ximenynic acid.

The saturated or unsaturated cyclic fatty acids having 6 to 30 carbon atoms, used in the present invention, mean saturated or unsaturated fatty acids having a cyclic structure in at least a portion of the basic skeleton and having 6 to 30 carbon atoms. Examples thereof include 9,10-methylene-9-octadecenoic acid, aleprylic acid, alepric acid, gorlic acid, α-cyclopentyl acid, α-cyclohexyl acid, α-cyclopentylethyl acid, α-cyclohexylmethyl acid, ω-cyclohexyl acid, 5(6)-carboxy-4-hexyl-2-cyclohexene-1-octanoic acid, malvalic acid, sterculynic acid, hydnocarpic acid, and chaulmoogric acid.

In the present invention, examples of the dextrin fatty acid ester prepared from the saturated branched fatty acids alone as the fatty acids include the followings:
dextrin isobutyric acid ester,
dextrin ethylmethylacetic acid ester,
dextrin isoheptanoic acid ester,
dextrin 2-ethylhexanoic acid ester,
dextrin isononanoic acid ester,
dextrin isodecanoic acid ester,
dextrin isopalmitic acid ester,
dextrin isostearic acid ester,
dextrin isoarachic acid ester,
dextrin isohexacosanoic acid ester, and
dextrin (isovaleric acid/isostearic acid) ester.

In the present invention, examples of the dextrin fatty acid ester prepared from a fatty acid mixture of the saturated branched fatty acids and the other fatty acids as the fatty acids include the followings:
dextrin (isobutyric acid/caprylic acid) ester,
dextrin (2-ethylhexanoic acid/caprylic acid) ester,
dextrin (isoarachic acid/caprylic acid) ester,
dextrin (isopalmitic acid/caprylic acid) ester,
dextrin (ethylmethylacetic acid/lauric acid) ester,
dextrin (2-ethylhexanoic acid/lauric acid) ester,
dextrin (isoheptanoic acid/lauric acid/behenic acid) ester
dextrin (isostearic acid/myristic acid) ester,
dextrin (isohexacosanoic acid/myristic acid) ester,
dextrin (2-ethylhexanoic acid/palmitic acid) ester,
dextrin (isostearic acid/palmitic acid) ester,
dextrin (isostearic acid/isovaleric acid/palmitic acid) ester,
dextrin (isononanoic acid/palmitic acid/caproic acid) ester,
dextrin (2-ethylhexanoic acid/palmitic acid/stearic acid) ester,
dextrin (isodecanoic acid/palmitic acid) ester,
dextrin (isopalmitic acid/stearic acid) ester,
dextrin (isostearic acid/arachic acid) ester,
dextrin (2-ethylhexanoic acid/arachic acid) ester,
dextrin (2-ethylbutyric acid/behenic acid) ester,
dextrin (isononanoic acid/linoleic acid) ester,
dextrin (isopalmitic acid/arachidonic acid) ester,
dextrin (isopalmitic acid/caprylic acid/linoleic acid) ester,
dextrin (isostearic acid/stearic acid/oleic acid) ester, and
dextrin (isoarachic acid/palmitic acid/chaulmoogric acid) ester.

(Method for Producing Dextrin Fatty Acid Ester)

Next, a method for producing the dextrin fatty acid ester of the present invention will be described.

A production method known in the art can be adopted without particular limitations in the present invention. For example, the dextrin fatty acid ester of the present invention can be produced as follows:

1) Dextrin having an average degree of glucose polymerization of 3 to 150 is reacted with fatty acid derivatives comprising more than 50 mol % and 100 mol % or less, based on the total amount of the fatty acid derivatives, of one or more saturated branched fatty acid derivatives having 4 to 26 carbon atoms and 0 mol % or more and less than 50 mol %, based on the total amount of the fatty acid derivatives, of one or more fatty acids selected from the group consisting of saturated linear fatty acid derivatives having 2 to 22 carbon atoms, unsaturated linear or branched fatty acid derivatives having 6 to 30 carbon atoms, and saturated or unsaturated cyclic fatty acid derivatives having 6 to 30 carbon atoms (hereinafter, these fatty acid derivatives are collectively referred to as "the other fatty acid derivatives").

2) Dextrin having an average degree of glucose polymerization of 3 to 150 is reacted with one or more saturated branched fatty acid derivatives having 4 to 26 carbon atoms, and subsequently, the product is reacted with the other fatty acid derivatives, wherein the one or more saturated branched fatty acid derivatives having 4 to 26 carbon atoms are used in an amount of more than 50 mol % and 100 mol % or less based on the total amount of the fatty acid derivatives, and the other fatty acid derivatives are used in an amount of 0 mol % or more and less than 50 mol % based on the total amount of the fatty acid derivatives.

In the present invention, for example, halides, acid anhydrides, or the like of the fatty acids described above are used as the fatty acid derivatives used in the esterification reaction with the dextrin.

In any of the cases 1) and 2), first, the dextrin is dispersed in a reaction solvent, and a catalyst is added thereto, if necessary. This mixture is reacted by the addition of halides, acid anhydrides, or the like of the fatty acids described above. In the production method 1), these acids are mixed and simultaneously added thereto for the reaction. In the production method 2), the saturated branched fatty acid derivatives, which are lower reactive, are first reacted therewith, and subsequently, the other fatty acid derivatives are added and reacted with the product.

Of them, a preferable method can be adopted for the production. For example, a formamide (e.g., dimethylformamide and formamide), acetamide, ketone, aromatic compound (e.g., benzene, toluene, and xylene), or dioxane solvent can be used appropriately as the reaction solvent. A tertiary amino compound such as pyridine or picoline can be used as the reaction catalyst. The reaction temperature is appropriately selected according to the starting fatty acids, etc., and is preferably a temperature of 0° C. to 100° C.

(Use)

Next, a composition containing the novel dextrin fatty acid ester of the present invention will be described in detail. When the novel dextrin fatty acid ester of the present invention is contained in a composition, its content is not particularly limited and is preferably 0.01 to 90% by mass, more preferably 0.1 to 50% by mass.

The composition containing the novel dextrin fatty acid ester of the present invention can be used as a base for cosmetics, pharmaceutical drugs, quasi drugs, stationery, ink, paint, and the like.

The composition can further contain appropriate acceptable ingredients according to the use.

For example, in the case of cosmetics, ingredients used in usual cosmetics, for example, oils, surfactants, alcohols, water, moisturizing agents, gelling agents and thickeners, powders, UV absorbers, antiseptics, antimicrobial agents, antioxidants, skin beautifying ingredients (skin-lightening agents, cellular stimulants, anti-inflammatory agents, blood circulation promoters, skin astringents, antiseborrheic agents, etc.), vitamins, amino acids, nucleic acids, hormones, can be contained therein without impairing the effects of the novel dextrin fatty acid ester of the present invention.

Examples of the oils include, but not particularly limited to, solid oil, semi-solid oil, and liquid oil and specifically include natural animal/plant oils and semisynthetic oils, hydrocarbon oils, ester oils, glyceride oils, silicone oils, higher alcohols, higher fatty acids, and organic solvents.

Examples of the solid oil include: natural waxes such as carnauba wax, candelilla wax, cotton wax, shellac wax, and hydrogenated oil; mineral-based waxes such as ozocerite, ceresin, paraffin wax, and microcrystalline wax; synthetic waxes such as polyethylene wax, Fischer-Tropsch wax, and ethylene-propylene copolymers; higher alcohols such as behenyl alcohol, cetyl alcohol, stearyl alcohol, cholesterol, and phytosterol; and higher fatty acids such as stearic acid and behenic acid.

Examples of the liquid oil specifically include natural animal/plant oils and semisynthetic oils such as avocado oil, flaxseed oil, almond oil, insect wax, perilla oil, olive oil, kaya oil, cod-liver oil, apricot kernel oil, wheat germ oil, sesame oil, rice germ oil, rice bran oil, sasanqua oil, safflower oil, Chinese paulownia oil, cinnamon oil, turtle oil, soybean oil, tea seed oil, camellia oil, evening primrose oil, corn oil, rapeseed oil, Japanese paulownia oil, rice bran wax, germ oil, persic oil, palm oil, palm kernel oil, castor oil, sunflower oil, grape seed oil, jojoba oil, macadamia nut oil, cottonseed oil, coconut oil, coconut fatty acid triglyceride, peanut oil, lanolin, liquid lanolin, reduced lanolin, lanolin alcohol, lanolin acetate, lanolin fatty acid isopropyl ester, POE lanolin alcohol ether, POE lanolin alcohol acetate, lanolin fatty acid polyethylene glycol, POE hydrogenated lanolin alcohol ether, and egg yolk oil.

Examples of the hydrocarbon oils include squalane, squalene, liquid paraffin, pristane, and polyisobutylene.

Examples of the ester oils include diisobutyl adipate, 2-hexyldecyl adipate, di-2-heptylundecyl adipate, N-alkyl glycol monoisostearate, isocetyl isostearate, trimethylolpropane triisostearate, cetyl 2-ethylhexanoate, ethylene glycol di-2-ethylhexanoate, neopentyl glycol di-2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, 2-octyldodecyl myristate, 2-hexyldecyl myristate, myristyl myristate, hexyldecyl dimethyloctanoate, ethyl laurate, hexyl laurate, N-lauroyl-L-glutamic acid-2-octyldodecyl ester, and diisostearyl malate.

Examples of the glyceride oils include acetoglyceride, glyceride triisooctanoate, glyceride triisostearate, glyceride triisopalmitate, glyceride tri-2-ethylhexanoate, glyceride monostearate, glyceride di-2-heptylundecanoate, and glyceride trimyristate.

Examples of the silicone oils include dimethylpolysiloxane, methylphenylpolysiloxane, methyl hydrogen polysiloxane, octamethylcyclotetrasiloxane, decamethylcyclopentasiloxane, dodecamethylcyclohexasiloxane, tetramethyl tetrahydrogen cyclotetrasiloxane, and alkyl-modified silicone.

Examples of the higher alcohols include oleyl alcohol, lauryl alcohol, stearyl alcohol, isostearyl alcohol, and 2-octyldodecanol.

Examples of the higher fatty acids include oleic acid, palmitic acid, myristic acid, stearic acid, and isostearic acid.

Examples of the organic solvents include: hydrocarbons such as n-hexane and cyclohexane; aromatic compounds such as benzene, toluene, and xylene; nonaromatic compounds such as ethyl acetate and butyl acetate; chlorine compounds such as chloroform, dichloromethane, and dichloroethane; ether compounds such as dioxane and tetrahydrofuran; and 2-propanol, benzyl alcohol, phenoxyethanol, carbitols, cellosolves, polybutene, and spindle oil.

Any surfactant usually used in cosmetics may be used without particular limitations. Examples of the surfactants include anionic surfactants, cationic surfactants, nonionic surfactants, and amphoteric surfactants. One of or a combination of two or more of them can be used according to the need.

Examples of the anionic surfactants specifically include fatty acid soaps (e.g., sodium stearate and triethanolamine palmitate), alkyl ether carboxylic acid and salts thereof, carboxylate obtained by condensation of amino acids and fatty acids or the like, alkylsulfonic acid, alkene sulfonate, sulfonate of fatty acid ester, sulfonate of fatty acid amide, alkyl sulfonate and sulfonate of formalin condensate thereof, sulfuric acid ester salts (e.g., alkyl sulfuric acid ester salt, secondary higher alcohol sulfuric acid ester salt, alkyl and aryl ether sulfuric acid ester salts, fatty acid ester sulfuric acid ester salts, sulfuric acid ester salt of fatty acid alkylol amide, polyoxyethylene alkyl sulfuric acid ester salt, and Turkey red oil), alkyl phosphate, ether phosphate, alkylaryl ether phosphate, amide phosphate, and N-acylamino acid surfactants.

Examples of the cationic surfactants include: alkyl-quaternary ammonium salts or aromatic quaternary ammonium salts such as long-chain alkyltrimethylammonium salt, di-long-chain alkyldimethylammonium salt, long-chain alkyldimethylbenzylammonium salt, di-polyoxyethylene alkylmethylammonium salt, di-polyoxyethylene alkyl ether dimethylammonium salt, polyoxypropylene methyldiethylammonium salt; pyridinium salts such as alkylpyridinium salt; imidazoline salts such as alkyl dihydroxyethyl imidazoline salt; N-acyl-basic amino acid lower alkyl ester salts; and amine salts such as alkylamine salt, polyamine, and amino alcohol fatty acid derivatives.

Examples of the nonionic surfactants include sorbitan fatty acid ester, glycerin fatty acid ester, polyglycerin fatty acid ester, propylene glycol fatty acid ester, polyethylene glycol fatty acid ester, sucrose fatty acid ester, polyoxyethylene alkyl ether, polyoxypropylene alkyl ether, polyoxyethylene alkylphenyl ether, polyoxyethylene fatty acid ester, polyoxyethylene sorbitan fatty acid ester, polyoxyethylene sorbitol fatty acid ester, polyoxyethylene glycerin fatty acid ester, polyoxyethylene propylene glycol fatty acid ester, polyoxyethylene castor oil, polyoxyethylene hydrogenated castor oil, polyoxyethylene hydrogenated castor oil fatty acid ester, polyoxyethylene phytostanol ether, polyoxyethylene phytosterol ether, polyoxyethylene cholestanol ether, polyoxyethylene cholesteryl ether, polyoxyalkylene-modified organopolysiloxane, polyoxyalkylene-alkyl-comodified organopolysiloxane, alkanolamide, sugar ether, and sugar amide.

Examples of the amphoteric surfactants include: carbobetaine-type amphoteric surfactants such as alkyldimethylaminoacetic acid betaine, fatty acid amide propyldimethylaminoacetic acid betaine, and alkyldihydroxyethylaminoacetic acid betaine; sulfobetaine-type amphoteric surfactants such as alkyl sulfobetaine; amidoamine (imidazoline)-type amphoteric surfactants such as N-fatty acid acyl-N-carboxymethyl-N-hydroxyethylethylenediamine salt and N-fatty acid acyl-N-carboxymethoxyethyl-N-carboxymethylethylenediamine disalt; amino acid-type amphoteric surfactants such as N-[3-alkyloxy-2-hydroxypropyl]arginine salt; and alkyliminodicarboxylate-type amphoteric surfactants.

Examples of the alcohols specifically include: lower alcohols such as ethanol and isopropanol; polyhydric alcohols such as glycerin, diglycerin, polyglycerin, diethylene glycol, polyethylene glycol, propylene glycol, dipropylene glycol, polypropylene glycol, 1,3-butylene glycol, and erythritol; and sugar alcohols such as sorbitol, maltose, xylitol, and maltitol.

Examples of the moisturizing agents include urea, hyaluronic acid, chondroitin sulfate, and pyrrolidone carboxylate.

Examples of the aqueous thickeners and gelling agents include: plant-derived polymers such as gum arabic, tragacanth gum, galactan, carob gum, guar gum, karaya gum, carrageenan, pectin, agar, quince seed (*Cyclonia oblonga*), starch (rice, corn, potato, and wheat starches), algal colloids, trant gum, and locust bean gum; microbe-derived polymers such as xanthan gum, dextran, succinoglycan, and pullulan; animal-derived polymers such as collagen, casein, albumin, and gelatin; starch polymers such as carboxymethyl starch and methylhydroxypropyl starch; cellulose polymers such as methylcellulose, ethylcellulose, hydroxypropylmethylcellulose, carboxymethylcellulose, hydroxymethylcellulose, hydroxypropylcellulose, nitrocellulose, sodium cellulose sulfate, sodium carboxymethylcellulose, crystalline cellulose, and cellulose powders; alginic acid polymers such as sodium alginate and alginic acid propylene glycol ester; vinyl polymer such as polyvinylmethyl ether, carboxyvinyl polymer, and alkyl-modified carboxyvinyl polymer; polyoxyethylene polymers; polyoxyethylene-polyoxypropylene copolymer-type polymers; acrylic polymer such as sodium polyacrylate, polyethyl acrylate, and polyacrylamide; inorganic thickeners such as bentonite, magnesium aluminum silicate, Laponite, Hectorite, and anhydrous silicic acid; polyethylenimine; and cationic polymers. Film-forming agents such as polyvinyl alcohol and polyvinylpyrrolidone are also included therein.

Examples of oil gelling agents include: metal soaps such as aluminum stearate, magnesium stearate, and zinc myristate; amino acid derivatives such as N-lauryol-L-glutamic acid and α,γ-di-n-butylamine; dextrin fatty acid esters such as dextrin palmitic acid ester and dextrin stearic acid ester; sucrose fatty acid esters such as sucrose palmitic acid ester and sucrose stearic acid ester; benzylidene derivatives of sorbitol such as monobenzylidene sorbitol and dibenzylidene sorbitol; and organically modified clay minerals such as dimethylbenzyldodecyl ammonium montmorillonite clay and dimethyldioctadecyl ammonium montmorillonite clay.

Examples of the powders include inorganic powders, organic powders, metal soap powders, colored pigments, pearl pigments, metal powders, tar dyes, and natural dyes. Any particle shape (e.g., spherical, needle-like, or plate-like shape), particle size (e.g., aerosol, fine particle, or pigment grade), and particle structure (e.g., porous or nonporous structure) can be used without limitations.

Examples of the inorganic powders specifically include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, lepidolite, silicic acid, anhydrous silicic acid, aluminum silicate, magnesium silicate, aluminum magnesium silicate, calcium silicate, barium silicate, strontium silicate, tungstic acid metal salt, hydroxyapatite, vermiculite, HIGILITE, bentonite, montmorillonite, hectorite, zeolite, ceramic powders, calcium hydrogen phosphate, alumina, aluminum hydroxide, boron nitride, and silica.

Examples of the organic powders include polyamide powders, poly ester powders, polyethylene powders, polypropylene powders, polystyrene powders, polyurethane, benzoguanamine powders, polymethylbenzoguanamine powders, tetrafluoroethylene powders, polymethyl methacrylate powders, cellulose powders, silk powders, nylon powders (nylon 12 and nylon 6), styrene-acrylic acid copolymer powders, divinylbenzene-styrene copolymer powders, vinyl resin powders, urea resin powders, phenol resin powders, fluorine resin powders, silicon resin powders, acrylic resin powders, melamine resin powders, epoxy resin powders, polycarbonate resin powders, microcrystalline fiber powders, rice starch, and lauroyl lysine.

Examples of the metal soap powders (surfactant metal salt powders) include powders of zinc stearate, aluminum stearate, calcium stearate, magnesium stearate, zinc myristate, magnesium myristate, zinc cetylphosphate, calcium cetylphosphate, and sodium zinc cetylphosphate.

Examples of the colored pigments include: inorganic red pigments such as iron oxide, iron hydroxide, and iron titanate; inorganic brown pigments such as γ-iron oxide; inorganic yellow pigments such as yellow iron oxide and loess; inorganic black pigments such as black iron oxide and carbon black; inorganic violet pigments such as manganese violet and cobalt violet; inorganic green pigments such as chromium hydroxide, chromium oxide, cobalt oxide, and cobalt titanate; inorganic blue pigments such as iron blue and ultramarine blue; and lake pigment from tar dyes, lake pigment from natural dyes, and composite powders thereof.

Examples of the pearl pigments include titanium oxide-coated mica, titanium oxide-coated mica, bismuth oxychloride, titanium oxide-coated bismuth oxychloride, titanium oxide-coated talc, pearl essence, and titanium oxide-coated colored mica. Also, examples of the metal powders include aluminum powders, copper powders, and stainless powders.

Examples of the tar dyes include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207. Examples of the natural dyes include carminic acid, laccaic acid, carthamin, brazilin, and crocin.

These powders may be used directly. Alternatively, a composite of these powders may be used, or these powders may be surface-treated with an oil solution, silicone, fluorine compound, or the like for use.

One of or a combination of two or more of these powders can be used according to the need.

Examples of the UV absorbers include: benzoic acid UV absorbers such as p-aminobenzoic acid; anthranilic acid UV absorbers such as methyl anthranilate; salicylic acid UV absorbers such as methyl salicylate; cinnamic acid UV absorbers such as octyl p-methoxycinnamate; benzophenone UV absorbers such as 2,4-dihydroxybenzophenone; and urocanic acid UV absorbers such as ethyl urocanate.

Examples of the antiseptics and antimicrobial agents include p-hydroxybenzoate ester, benzoic acid, sodium benzoate, sorbic acid, potassium sorbate, phenoxyethanol, salicylic acid, carbolic acid, sorbic acid, parachlorometacresol, hexachlorophene, benzalkonium chloride, chlorhexidine chloride, trichlorocarbanilide, photosensitizing dyes, and isopropylmethylphenol.

Examples of the antioxidants include tocopherol, butylhydroxyanisole, and dibutylhydroxytoluene. Examples of the pH adjusters include lactic acid, lactate, citric acid, citrate, glycolic acid, succinic acid, tartaric acid, malic acid, potassium carbonate, sodium bicarbonate, and ammonium bicarbonate. Examples of the chelating agents include alanine, sodium edetate, sodium polyphosphate, sodium metaphosphate, phosphate, and hydroxyethane diphosphone. Examples of the algefacients include L-menthol, camphor, mint oil, peppermint oil, and eucalyptus oil. Examples of the anti-inflammatory agents include allantoin, glycyrrhetinate, glycyrrhizin derivatives, tranexamic acid, and azulene.

Examples of the skin beautifying ingredients include: skin-lightening agents such as arbutin, glutathione, and strawberry geranium extracts; cellular stimulants such as royal jelly, sensitizing dyes, cholesterol derivatives, and extracts from hemolysed blood of young calves; rough skin-improving agents; blood circulation promoters such as nonylic acid vanillylamide, nicotinic acid benzyl ester, nicotinic acid β-butoxyethyl ester, capsaicin, zingerone, cantharides tincture, ichthammol, caffeine, tannic acid, α-borneol, tocopherol nicotinate, inositol hexanicotinate, cyclandelate, cinnarizine, tolazoline, acetylcholine, verapamil, cepharanthine, and γ-oryzanol; skin astringents such as zinc oxide and tannic acid; and antiseborrheic agents such as sulfur and thianthol.

Examples of the vitamins include vitamins A such as vitamin A oil, retinol, retinol acetate, and retinol palmitate; vitamins B2 such as riboflavin, riboflavin butyrate, and flavin adenine nucleotide; vitamins B6 such as pyridoxine hydrochloride and pyridoxine dioctanoate; vitamins C such as L-ascorbic acid, L-ascorbic acid dipalmitic acid ester, sodium L-ascorbic acid-2-sulfate, and dipotassium dl-α-tocopherol-L-ascorbic acid phosphoric acid diester; pantothenic acids such as calcium pantothenate, D-pantothenyl alcohol, pantothenyl ethyl ether, acetyl and pantothenyl ethyl ether; vitamins D such as ergocalciferol and cholecalciferol; nicotinic acids such as nicotinic acid, benzyl nicotinate, and nicotinic acid amide; vitamins E such as dl-α-tocopherol, dl-α-tocopherol acetate, dl-α-tocopherol nicotinate, and dl-α-tocopherol succinate; vitamin P; and biotin.

Examples of the amino acids include arginine, aspartic acid, cystine, cysteine, methionine, serine, leucine, isoleucine, tryptophan, alanine, glycine, and proline. Examples of the nucleic acids include deoxyribonucleic acids. Examples of the hormones include estradiol and ethinylestradiol.

When the dextrin fatty acid ester of the present invention is used in cosmetics, the cosmetics can be prepared in various forms, for example, liquid, emulsion, cream, solid, gel, and paste forms, by a routine method using the dextrin fatty acid ester in combination with other ingredients according to the need. The cosmetic containing the dextrin fatty acid ester of the present invention may be in any of dosage forms such as oils, water-in-oil-type emulsions, or oil-in-water-type emulsions, without particular limitations as long as the dosage form can contain oil ingredients. Specifically, various products can be achieved, for example, skincare cosmetics such as skin milks, creams, skin essences, cosmetic oils, lip creams, hand creams, and face washes, makeup cosmetics such as foundations, makeup bases, cheek colors, eye shadows, mascaras, eye liners, eyebrow makeups, overcoats, lipsticks, and lip grosses, and cosmetics for scalp or hair such as hair tonics, hair creams, shampoos, rinses, conditioners, and hair styling agents.

EXAMPLES

Hereinafter, Examples will be shown. However, the present invention is not intended to be limited to these Examples.

Production Examples of Dextrin Fatty Acid Ester

Production Example 1

Dextrin Isostearic Acid (Emery Type) Ester 21.41 g (0.132 mol) of dextrin having an average degree of glucose polymerization of 30 was dispersed at 70° C. in a mixed solvent consisting of 71 g of dimethylformamide and 62 g (0.666 mol) of 3-methylpyridine, and 120 g (0.396 mol) of isostearic acid chloride (Emery type) was added dropwise thereto over 30 minutes. After the completion of dropwise addition, the mixture was reacted with the reaction temperature set to 80° C. for 5 hours. After the completion of reaction, the reaction solution was dispersed in methanol, and the upper layer was removed. Semi-solid matter was washed several times with methanol and then dried to obtain 107 g of a pale yellow resinous substance.

FIG. 1 shows the IR spectrum of the obtained dextrin isostearic acid (Emery type) ester.

From this IR spectrum, dextrin-derived peaks were confirmed at 1000 to 1200 $cm^{-1}$; an ester-derived peak was confirmed at 1742 $cm^{-1}$; and alkyl-derived peaks were confirmed at 2800 to 3000 $cm^{-1}$. From the amount of fatty acids after alkaline decomposition and gas chromatography results, this ester was confirmed to have a degree of substitution of 2.2 and contain 60 mol % of isostearic acid and 40 mol % of the other fatty acids (including 10 mol % of palmitic acid).

Production Examples 2 to 4

Dextrin Isostearic Acid (Emery Type) Ester

According to the materials and the method described in Production Example 1, in Production Example 2, dextrin isostearic acid (Emery type) ester having a degree of substitution of 1.0 was obtained using 0.132 mol of dextrin having an average degree of glucose polymerization of 30 and 0.172 mol of isostearic acid chloride (Emery type). In Production Example 3, dextrin isostearic acid (Emery type) ester having a degree of substitution of 1.4 was obtained using 0.132 mol of dextrin having an average degree of glucose polymerization of 30 and 0.224 mol of isostearic acid chloride (Emery type). In Production Example 4, dextrin isostearic acid (Emery type) ester having a degree of substitution of 2.6 was obtained using 0.132 mol of dextrin having an average degree of glucose polymerization of 30 and 0.502 mol of isostearic acid chloride (Emery type).

Production Example 5

Dextrin Isostearic Acid Ester 80 g of a pale yellow resinous substance was obtained by the same preparation procedures as in Production Example 1 except that isostearic acid chloride (Guerbet reaction type) was used instead of isostearic acid chloride (Emery type). As a result of measurement in the same way as in Production Example 1, the degree of substitution was 1.8.

Production Example 6

Dextrin Isostearic Acid Ester 60 g of a pale yellow resinous substance was obtained by the same preparation procedures as in Production Example 1 except that isostearic acid chloride (aldol condensation type) was used instead of isostearic acid chloride (Emery type). As a result of measurement in the same way as in Production Example 1, the degree of substitution was 1.2.

Production Example 7

Dextrin Isoarachic Acid/Palmitic Acid Ester 51.28 g of dextrin having an average degree of glucose polymerization of 150 was dispersed at 70° C. in a mixed solvent consisting of 150 g of dimethylformamide and 60 g of pyridine, and a mixture of 132 g of isoarachic acid chloride and 12 g of palmitic acid chloride was added dropwise thereto over 30 minutes. After the completion of dropwise addition, the mixture was reacted with the reaction temperature set to 80° C. for 5 hours. After the completion of reaction, the reaction solution was dispersed in methanol, and the upper layer was removed. Semi-solid matter was washed several times with methanol and then dried to obtain 145 g of a pale yellow resinous substance. As a result of measurement in the same way as in Production Example 1, this ester had a degree of substitution of 1.1 and contained 85 mol % of isoarachic acid and 15 mol % of palmitic acid.

Production Example 8

Dextrin Isobutyric Acid/Capric Acid Ester 34.19 g of dextrin having an average degree of glucose polymerization of 5 was dispersed at 70° C. in 215 g of 3-methylpyridine, and a mixture of 50 g of isobutyric acid chloride and 60 g of capric acid chloride was added dropwise thereto over 30 minutes. After the completion of dropwise addition, the mixture was reacted with the reaction temperature set to 80° C. for 5 hours. After the completion of reaction, the reaction solution was dispersed in methanol, and the upper layer was removed. Semi-solid matter was washed several times with ethanol and then dried to obtain 98 g of a pale yellow resinous substance. As a result of measurement in the same way as in Production Example 1, this ester had a degree of substitution of 2.9 and contained 63 mol % of isobutyric acid and 37 mol % of capric acid.

Production Example 9

Dextrin Isopalmitic Acid Ester 23.62 g of dextrin having an average degree of glucose polymerization of 100 was dispersed at 70° C. in a mixed solvent consisting of 71 g of dimethylformamide and 62 g of 3-methylpyridine, and 100 g of isopalmitic acid chloride was added dropwise thereto over 30 minutes. After the completion of dropwise addition, the mixture was reacted with the reaction temperature set to 80° C. for 5 hours. After the completion of reaction, the reaction solution was dispersed in methanol, and the upper layer was removed. Semi-solid matter was washed several times with methanol and then dried to obtain 90 g of a pale yellow resinous substance. As a result of measurement in the same way as in Production Example 1, the degree of substitution was 2.0.

Production Example 10

Dextrin Isononanoic Acid/Stearic Acid Ester 36.34 g of dextrin having an average degree of glucose polymerization of 20 was dispersed at 70° C. in a mixed solvent consisting of 120 g of dimethylformamide and 62 g of 3-methylpyridine, and a mixture of 41 g of isononanoic acid chloride and 58 g of stearic acid chloride was added dropwise thereto over 30 minutes. After the completion of dropwise addition, the mixture was reacted with the reaction temperature set to 80° C. for 5 hours. After the completion of reaction, the reaction solution was dispersed in methanol, and the upper layer was removed. Semi-solid matter was washed several times with methanol and then dried to obtain 95 g of a pale yellow resinous substance. As a result of measurement in the same way as in Production Example 1, this ester had a degree of substitution of 1.6 and contained 51 mol % of isononanoic acid and 49 mol % of stearic acid.

Production Example 11

Dextrin 2-Ethylhexanoic Acid/Behenic Acid Ester 54.56 g of dextrin having an average degree of glucose polymerization of 20 was dispersed at 70° C. in a mixed solvent consisting of 150 g of dimethylformamide and 130 g of 3-methylpyridine, and 147 g of 2-ethylhexanoic acid chloride and subsequently 36 g of behenic acid chloride were added dropwise thereto over 30 minutes in total. After the completion of dropwise addition, the mixture was reacted with the reaction temperature set to 80° C. for 5 hours. After the completion of reaction, the reaction solution was dispersed in methanol, and the upper layer was removed. Semi-solid matter was washed several times with methanol and then dried to obtain 95 g of a pale yellow resinous substance. As a result of measurement in the same way as in Production Example 1, this ester had a degree of substitution of 2.3 and contained 95 mol % of 2-ethylhexanoic acid and 5 mol % of behenic acid.

Production Example 12

Dextrin Isopalmitic Acid/Acetic Acid Ester 22.56 g of dextrin having an average degree of glucose polymerization of 20 was dispersed at 70° C. in a mixed solvent consisting of 71 g of dimethylformamide and 70 g of 3-methylpyridine, and a mixture of 110 g of isopalmitic acid chloride and 10 g of acetic anhydride was added dropwise thereto over 30 minutes. After the completion of dropwise addition, the mixture was reacted with the reaction temperature set to 80° C. for 5 hours. After the completion of reaction, the reaction solution was dispersed in methanol, and the upper layer was removed. Semi-solid matter was washed several times with methanol and then dried to obtain 96 g of a pale yellow resinous substance. As a result of measurement in the same way as in Production Example 1, this ester had a degree of substitution of 2.8 and contained 79 mol % of isopalmitic acid and 21 mol % of acetic acid.

Production Example 13

Dextrin Isostearic Acid (Emery Type)/Oleic Acid Ester 19.99 g of dextrin having an average degree of glucose polymerization of 40 was dispersed at 70° C. in a mixed solvent consisting of 71 g of dimethylformamide and 62 g of 3-methylpyridine, and a mixture of 108 g of isostearic acid chloride (Emery type) and 12 g of oleic acid chloride was added dropwise thereto over 30 minutes. After the completion of dropwise addition, the mixture was reacted with the reaction temperature set to 80° C. for 5 hours. After the completion of reaction, the reaction solution was dispersed in methanol, and the upper layer was removed. Semi-solid matter was washed several times with methanol and then dried to obtain 88 g of a pale yellow resinous substance. As a result of measurement in the same way as in Production Example 1, this ester had a degree of substitution of 2.2 and contained 54 mol % of isostearic acid and 46 mol % of the other fatty acids (including 10 mol % of oleic acid).

Comparative Examples 1 to 3

Dextrin palmitic acid ester of Comparative Example 1 (degree of substitution: 2.2) and dextrin palmitic acid ester of Comparative Example 2 (degree of substitution: 1.5) containing 100 mol % of linear fatty acids were obtained in the same way as in Production Example 1 except that palmitic acid chloride was used instead of isostearic acid chloride described in Production Example 1; and the number of moles in reaction was changed. Likewise, dextrin 2-ethylhexanoic acid/palmitic acid ester of Comparative Example 3 (degree of substitution: 1.5) containing 25 mol % of saturated branched fatty acids and 75 mol % of saturated linear fatty acids was obtained in the same way as above using 2-ethylhexanoic acid chloride and palmitic acid chloride.

<<Tackiness/Viscosity Measurement Results>>

Tackiness and viscosity were measured by methods shown below for the dextrin fatty acid esters produced in Production Examples 1 to 13 and Comparative Examples 1 to 3, trimethylsiloxysilicate (Comparative Example 4), and pentaerythritol rosinate (Comparative Example 5). The results are shown in Table 1.

(Tackiness Evaluation Method)

A solution containing 40% of each sample dissolved in IP Clean LX (light liquid isoparaffin) was applied at a thickness of 400 μm on a glass plate using an applicator, and the film was dried at room temperature for 24 hours and then stored at 70° C. for 12 hours. Then, the tackiness at room temperature (25° C.) was evaluated using the following equipment and conditions:

[Measuring equipment] Texture analyzer TA.XTplus (manufactured by Stable Micro Systems Ltd.)

[Probe] ½ Cyl. Delrin (polyacetal resin (POM)) P/0.5), diameter: 12.5 mm, cylindrical

[Measurement conditions] Test Speed: 0.5 mm/sec, Applied Force: 100 g, Contact Time: 10 sec (Viscosity Evaluation)

Liquid paraffin containing 5% by mass of each sample was dissolved at 100° C. and cooled to room temperature (25° C.). After incubation for 24 hours in a thermostat of 25° C., the viscosity was measured using measuring equipment shown below.

The liquid paraffin used had a kinematic viscosity at 40° C. of 8 mm$^2$/s as measured by ASTM D445 test method. [Measuring equipment] Yamco DIGITAL VISCOMATE MODEL VM-100A (manufactured by Yamaichi Electronics Co., Ltd.)

TABLE 1

| | | Production Example | | | | | | | | |
|---|---|---|---|---|---|---|---|---|---|---|
| | | 1 | 2 | 3 | 4 | 5 | 6 | 7 | 8 | 9 |
| Dextrin fatty acid ester | Degree of polymerization in dextrin (n) | 30 | 30 | 30 | 30 | 30 | 30 | 150 | 5 | 100 |
| | Type of saturated branched fatty acids having 4 to 26 carbon atoms | C18*[1] | C18*[1] | C18*[1] | C18*[1] | C18*[2] | C18*[3] | C20*[4] | C4 | C16*[5] |
| | Type of the other fatty acids | C16 (saturated linear), etc. | C16 (saturated linear), etc. | C16 (saturated linear), etc. | C16 (saturated linear), etc. | — | — | C16 (saturated linear) | C10 (saturated linear) | — |
| | Saturated branched fatty acids added mol % | 60 | 60 | 60 | 60 | 100 | 100 | 90 | 60 | 100 |
| | Degree of substitution per unit in dextrin mol | 2.2 | 1.0 | 1.4 | 2.6 | 1.8 | 1.2 | 1.1 | 2.9 | 2 |
| | Saturated branched fatty acids substituted therefor mol % | 60 | 60 | 60 | 60 | 100 | 100 | 85 | 63 | 100 |

TABLE 1-continued

|  |  | | | | | | | | | |
|---|---|---|---|---|---|---|---|---|---|---|
| Others | Trimethylsiloxysilicate*⁷ | — | — | — | — | — | — | — | — | — |
|  | Pentaerythritol rosinate*⁸ | — | — | — | — | — | — | — | — | — |
| Results | Tackiness maximum stress value n = 3 (g) | 161 | 35 | 45 | 750 | 173 | 61 | 45 | 255 | 204 |
|  | Viscosity value mPa·s (25° C.) | 0 | 0 | 0 | 0 | 0 | 0 | 0 | 0 | 0 |

|  |  | Production Example | | | | Comparative Example | | | | |
|---|---|---|---|---|---|---|---|---|---|---|
|  |  | 10 | 11 | 12 | 13 | 1 | 2 | 3 | 4 | 5 |
| Dextrin fatty acid ester | Degree of polymerization in dextrin (n) | 20 | 20 | 20 | 40 | 30 | 30 | 30 | — | — |
|  | Type of saturated branched fatty acids having 4 to 26 carbon atoms | C9*⁶ | C8 | C16 | C18*¹ | — | — | C8 | — | — |
|  | Type of the other fatty acids | C18 (saturated linear) | C22 (saturated linear) | C1 (saturated linear) | C18 (unsaturated linear), etc. | C16 (saturated linear) | C16 (saturated linear) | C16 (saturated linear) | — | — |
|  | Saturated branched fatty acids added mol % | 55 | 90 | 80 | 54 | 0 | 0 | 25 | — | — |
|  | Degree of substitution per unit in dextrin mol | 1.6 | 2.3 | 2.8 | 2.2 | 2.2 | 1.5 | 1.5 | — | — |
|  | Saturated branched fatty acids substituted therefor mol % | 51 | 95 | 79 | 54 | 0 | 0 | 13 | — | — |
| Others | Trimethylsiloxysilicate*⁷ | — | — | — | — | — | — | — | ○ | — |
|  | Pentaerythritol rosinate*⁸ | — | — | — | — | — | — | — | — | ○ |
| Results | Tackiness maximum stress value n = 3 (g) | 64 | 138 | 430 | 350 | 3 | 1 | 5 | 0.2 | 0.3 |
|  | Viscosity value mPa·s (25° C.) | 0 | 0 | 0 | 0 | 716 | 151 | 97 | 0 | 0 |

*¹Emery type (starting material: EMARSOL 873, Cognis Corp.)
*²Guerbet reaction type (starting material: FINEOXOCOL isostearic acid-N manufactured by Nissan Chemical Industries, Ltd.)
*³Aldol condensation type (starting material: FINEOXOCOL isostearic acid manufactured by Nissan Chemical Industries, Ltd.)
*⁴Isoarachic acid (starting material: isoarachic acid manufactured by Nissan Chemical Industries, Ltd.)
*⁵Isopalmitic acid (starting material: isopalmitic acid manufactured by Nissan Chemical Industries, Ltd.)
*⁶Isononanoic acid (starting material: KYOWANOIC N 3,5,5-trimethylhexanoic acid manufactured by Kyowa Hakko Chemical Co., Ltd.)
*⁷Silicone KF-7312J (manufactured by Shin-Etsu Chemical Co., Ltd.)
*⁸Ester Gum HP (manufactured by Arakawa Chemical Industries, Ltd.)

As described above, the features of the dextrin fatty acid ester of the present invention are that it has tackiness that has not previously been achieved, is superior in adhesion, and forms a film without causing gelation of liquid paraffin having a viscosity at 40° C. of 8 mm²/s as measured by ASTM D445 test method.

Formulation Examples of Composition Containing Dextrin Fatty Acid Ester

The dextrin fatty acid ester of the present invention produced in any of Production Examples above was used to prepare cosmetics shown below.

Formulation Example 1

Liquid Foundation

A liquid foundation was prepared according to the following composition and production method:

| (Ingredient) | (% by mass) |
|---|---|
| 1. Dextrin fatty acid ester of the present invention (Production Example 1) | 3 |
| 2. Decamethylcyclopentasiloxane | 7 |
| 3. Diisostearyl malate | 2 |
| 4. Liquid paraffin | 5 |
| 5. Octyldodecyl myristate | 5 |
| 6. Inulin stearic acid ester (*1) | 3 |
| 7. Dimethylpolysiloxane (*2) | 7 |
| 8. Branched silicone-type polyether-modified silicone (*3) | 2 |
| 9. Organically modified bentonite (*4) | 1 |
| 10. Spherical silica | 5 |
| 11. Titanium oxide | 7 |
| 12. Fine particle titanium oxide | 2 |
| 13. red iron oxide (Colcothar) | 0.2 |
| 14. Yellow iron oxide | 1 |
| 15. Black iron oxide | 0.2 |
| 16. Talc | 3 |
| 17. 1,3-butylene glycol | 3 |
| 18. Ethanol | 5 |
| 19. Antiseptic (methyl parahydroxybenzoate) | 0.1 |
| 20. Purified water | balance |
| 21. Fragrance | 0.1 |

(*1): Rheopearl ISL2 (manufactured by Chiba Flour Milling Co., Ltd.)
(*2): KF96A-6cs (manufactured by Shin-Etsu Chemical Co., Ltd.)
(*3): KF-6028P (manufactured by Shin-Etsu Chemical Co., Ltd.)
(*4): BENTONE 38 V (manufactured by Elementis plc)

[Production Method]

A: Ingredients 1 to 2 were uniformly dissolved by mixing.

B: Ingredients 3 to 8 were dissolved by heating.

C: Ingredients 9 to 16 were mixed and dispersed into the solution of B.

D: Ingredients 17 to 20 were uniformly mixed.

E: The mixture of D was added to the mixture of C at 60° C. for emulsification.

F: After cooling, the solution of A and ingredient 21 were added and mixed into the emulsion of E to obtain a liquid foundation.

The liquid foundation of Formulation Example 1 thus obtained offered smooth texture and was very excellent in adhesion and favorably durable.

Also, liquid foundations were obtained using the dextrin fatty acid esters of Production Examples 2 to 13 instead of the dextrin fatty acid ester of the present invention (Production Example 1) as ingredient 1. The obtained liquid foundations also offered smooth texture and were very excellent in adhesion and favorably durable.

By contrast, a liquid foundation was obtained using the dextrin fatty acid ester of Comparative Example 1 instead of the dextrin fatty acid ester of the present invention (Production Example 1) as ingredient 1. The obtained liquid foundation lacked adhesion and was poorly durable.

Furthermore, a liquid foundation obtained using the dextrin fatty acid ester of Comparative Example 2 lacked adhesion and was thus inferior in uniformity in the film of the liquid foundation.

Furthermore, a liquid foundation obtained using the dextrin fatty acid ester of Comparative Example 3 offered smooth texture, but lacked adhesion and was thus inferior in uniformity in the film of the liquid foundation.

In addition, a liquid foundation obtained using the substance of Comparative Example 4 offered poor texture due to very heavy texture and a lack of adhesion.

Formulation Example 2

Water-in-Oil-Type Sunscreen Cream

| (Ingredient) | (% by mass) |
| --- | --- |
| 1. Methyl trimethicone (*5) | 5 |
| 2. Acrylic silicone-treated fine particle titanium oxide (*6) | 5 |
| 3. Branched silicone-type lauryl/polyether-modified silicone (*7) | 0.5 |
| 4. Dimethylpolysiloxane (*8) | 2 |
| 5. Dextrin fatty acid ester of the present invention (Production Example 3) | 5 |
| 6. Octyl p-methoxycinnamate | 3 |
| 7. Cetyl isooctanoate | 5 |
| 8. Branched silicone-type polyether-modified silicone (*3) | 2 |
| 9. Ethanol | 7 |
| 10. Glycerin | 2 |
| 11. Sodium chloride | 1 |
| 12. Antiseptic (methyl parahydroxybenzoate) | 0.1 |
| 13. Silicone powder (*9) | 2 |
| 14. Fragrance | 0.05 |
| 15. Purified water | balance |

(*5): TMF-1.5 (manufactured by Shin-Etsu Chemical Co., Ltd.)
(*6): Fine particle titanium oxide treated with 3% of KP-549 (manufactured by Shin-Etsu Chemical Co., Ltd.)
(*7): KF-6038(manufactured by Shin-Etsu Chemical Co., Ltd.)
(*8): KF-96-2cs (manufactured by Shin-Etsu Chemical Co., Ltd.)
(*9): KSP-100 (manufactured by Shin-Etsu Chemical Co., Ltd.)

[Production Method]

A: Ingredients 1 to 3 are uniformly dispersed by bead mill treatment.

B: Ingredients 4 to 8 are dissolved by heating and uniformly mixed with the dispersion of A and ingredient 13.

C: Ingredients 9 to 12 and ingredient 15 are dissolved by mixing.

D: The mixture of B is emulsified by the addition of the solution of C and then cooled.

E: Ingredient 14 was added to the emulsion of D and uniformly mixed to obtain a water-in-oil-type sunscreen cream.

The obtained water-in-oil-type sunscreen cream of the present invention offered smooth texture and was very excellent in adhesion and favorably durable.

Formulation Example 3

Hair Cream

| (Ingredient) | (% by mass) |
| --- | --- |
| 1. Cetanol | 1 |
| 2. Behenyl alcohol | 1.5 |
| 3. Sorbitan sesquioleate | 1 |
| 4. Isotridecyl isononanoate | 2 |
| 5. Dextrin fatty acid ester of the present invention (Production Example 6) | 2 |
| 6. Dimethylpolysiloxane (*10) | 2 |
| 7. Decamethylcyclopentasiloxane | 5 |
| 8. Propylene glycol | 5 |
| 9. Ethanol | 5 |
| 10. Cationized cellulose (*11) | 0.1 |
| 11. Xanthan gum (*12) | 0.1 |
| 12. Antiseptic (methyl parahydroxybenzoate) | 0.1 |
| 13. Purified water | balance |
| 14. Fragrance | 0.05 |

(*10): KF-96-100cs (manufactured by Shin-Etsu Chemical Co., Ltd.)
(*11): Polymer JR400 (manufactured by Union Carbide Corp.)
(*12): KELTROL (manufactured by Kelco Company)

[Production Method]

A: Ingredients 1 to 8 are heated and uniformly mixed.

B: Ingredients 10 to 13 are heated and uniformly mixed.

C: The mixture of A is emulsified by the addition of the mixture of B at 80° C.

D: After cooling, ingredients 9 and 14 were added to the emulsion of C and uniformly mixed to obtain a hair cream.

The obtained hair cream of the present invention was smoothly spreadable when applied to hair, was very excellent in adhesion, made hair excellently glossy and manageable, and was favorably durable.

Formulation Example 4

Hair Mist (Hair Lotion)

| (Ingredient) | (% by mass) |
| --- | --- |
| 1. Propylene glycol | 1 |
| 2. Stearoyl trimethyl ammonium chloride | 0.3 |
| 3. Dicocoyl methyl ammonium chloride | 0.2 |
| 4. Dextrin fatty acid ester of the present invention (Production Example 9) | 2 |
| 5. Ethanol | 10 |
| 6. Hydroxyethylcellulose | 0.1 |
| 7. Antiseptic (1,2-pentanediol) | 3 |
| 8. Purified water | balance |
| 9. Fragrance | 0.03 |

[Production Method]

A: Ingredients 1 to 3 are heated and uniformly mixed.

B: Ingredients 4 to 9 are added to the mixture of A and uniformly mixed.

C: The mixture of B was charged into a dispenser container to obtain a hair mist (hair lotion).

The obtained hair mist (hair lotion) of the present invention made hair moderately glossy and excellently manageable when sprayed to hair, and was excellently durable.

Formulation Example 5

Oil-in-Water Emulsion-Type Eye Liner

| (Ingredient) | (% by mass) |
|---|---|
| 1. Stearic acid | 1 |
| 2. Cetanol | 1 |
| 3. Glycerin monostearate | 0.5 |
| 4. Ethylene glycol monostearate | 0.5 |
| 5. Polyoxyethylene-modified beeswax (*13) | 4 |
| 6. Dextrin fatty acid ester of the present invention (Production Example 2) | 0.5 |
| 7. Glycerin | 1 |
| 8. Black iron oxide | 15 |
| 9. Purified water | balance |
| 10. 1,3-butylene glycol | 5 |
| 11. Sodium hydroxide | 0.2 |
| 12. Antiseptic (methyl parahydroxybenzoate) | 0.1 |
| 13. Alkyl acrylate copolymer emulsion (*14) | 10 |
| 14. Titanated mica | 1 |
| 15. Fragrance | 0.05 |

(*13): Risorex BW400 (manufactured by Kokyu Alcohol Kogyo Co., Ltd.)
(*14): YODOSOL GH800F (45% solid content) (manufactured by Akzo Nobel)

[Production Method]

A. Ingredients 1 to 7 are dissolved by heating at 90° C., and ingredient 8 is added thereto and uniformly mixed.

B. Ingredients 9 to 15 are dissolved by heating at 80° C. and uniformly mixed.

C. The mixture of B is added to the mixture of A and emulsified at 80° C.

D. The emulsion is charged into a container to prepare a product.

The obtained oil-in-water emulsion-type eye liner of the present invention achieved easy drawing of lines and was excellently fitted to the skin.

Formulation Example 6

Skin Lotion

| (Ingredient) | (% by mass) |
|---|---|
| 1. Dipropylene glycol | 10 |
| 2. 1,3-butylene glycol | 9 |
| 3. Glycerin | 3 |
| 4. Hydrogenated lecithin | 0.4 |
| 5. Cholesterol | 0.1 |
| 6. Dipentaerythrityl hexa(hydroxystearate/stearate/rosinate) | 0.1 |
| 7. Dimethylpolysiloxane (*2) | 0.1 |
| 8. Jojoba oil | 0.1 |
| 9. Dextrin fatty acid ester of the present invention (Production Example 4) | 0.02 |
| 10. Water | balance |
| 11. EDTA-2Na | 0.01 |
| 12. (Acrylic acid/alkyl acrylate (C10 to 30)) copolymer | 0.1 |
| 13. Carrageenan | 0.04 |
| 14. Sodium hydroxide | 0.03 |
| 15. Ethanol | 1 |
| 16. Fragrance | 0.03 |
| 17. Antiseptic (phenoxyethanol) | 0.1 |

[Production Method]

A. Ingredients 1 to 5 are dissolved by heating at 90° C. and uniformly mixed.

B. Ingredients 6 to 9 are dissolved by heating at 80° C. and uniformly mixed.

C. Ingredients 10 to 13 are uniformly swollen.

D. The mixture of B is added to the mixture of A, the mixture of C is added thereto, and the resulting mixture is emulsified at 80° C., followed by addition of ingredients 14 to 17.

E. The mixture is charged into a container to prepare a product.

The obtained skin lotion of the present invention was excellently fitted to the skin to make the skin elastic.

Formulation Example 7

Oil-in-Water-Type Eye Cream

| (Ingredient) | (% by mass) |
|---|---|
| 1. Sodium N-stearoyl-N-methyltaurine | 0.8 |
| 2. EDTA-2Na | 0.01 |
| 3. Water | balance |
| 4. Antiseptic (methyl parahydroxybenzoate) | 0.05 |
| 5. 1,3-butylene glycol | 10 |
| 6. Glycerin | 8 |
| 7. Glycosyl trehalose | 4 |
| 8. Hydrogenated lecithin | 0.5 |
| 9. Cetostearyl alcohol | 3.5 |
| 10. Behenyl alcohol | 2 |
| 11. Glyceryl tri-2-ethylhexanoate | 5 |
| 12. Dextrin fatty acid ester of the present invention (Production Example 7) | 3 |
| 13. Squalane | 2 |
| 14. Dipentaerythrityl Hexa(hydroxystearate/stearate/rosinate) | 4 |
| 15. Heavy liquid isoparaffin | 5 |
| 16. Dimethylpolysiloxane (*10) | 0.1 |
| 17. Xanthan gum (*12) | 0.1 |
| 18. Water | 5 |
| 19. Ethanol | 4 |

[Production Method]

A. Ingredients 1 to 7 are dissolved by heating at 90° C. and uniformly mixed.

B. Ingredients 8 to 16 are dissolved by heating at 80° C. and uniformly mixed.

C. Ingredients 17 to 18 are uniformly swollen.

D. The mixture of B is added to the mixture of A, the mixture of C is added thereto, and the resulting mixture is emulsified at 80° C., followed by addition of ingredient 19.

E. The mixture is charged into a container to prepare a product.

The obtained oil-in-water-type eye cream of the present invention was fitted to the skin to make the skin elastic and soft.

Formulation Example 8

Nail Enamel

| (Ingredient) | (% by mass) |
|---|---|
| 1. Nitrocellulose | 10 |
| 2. Toluene sulfonamide expoxy resin (*15) | 5 |
| 3. Alkyl acrylate-styrene copolymer (*16) | 5 |
| 4. Acetyl tributyl citrate | 5 |
| 5. Dextrin fatty acid ester of the present invention (Production Example 8) | 1 |
| 6. Ethyl acetate | 20 |
| 7. Butyl acetate | balance |
| 8. Isopropyl alcohol | 5 |
| 9. Ethanol | 2 |
| 10. Butanol | 2 |
| 11. dl-camphor | 3 |
| 12. Red No. 220 | 0.1 |
| 13. Titanium oxide | 0.5 |
| 14. Titanated mica (*17) | 10 |
| 15. 2-ethylhexyl p-methoxycinnamate | 0.5 |
| 16. Oxybenzone | 0.5 |
| 17. Organically modified bentonite (*18) | 1 |
| 18. Anhydrous silicic acid (*19) | 0.5 |

(*15): NAGELLITE 3050 (manufactured by Telechemische Inc.)
(*16): Acrybase MH7057 (manufactured by Fujikura Kasei Co., Ltd.)
(*17): Timiron Supersheen MP-1001 (manufactured by Merck)
(*18): Bentone 27 (manufactured by NL Industries, Inc.)
(*19): Aerosil 300 (manufactured by Nippon Aerosil Co., Ltd.)

[Production Method]
A: Ingredients 1 to 5 are added to ingredients 6 to 11 and dissolved using Disper.
B: Ingredients 12 to 18 were further added thereto and uniformly mixed and dispersed using Disper, and the resulting mixture was charged into a container to obtain a nail enamel.

The obtained nail enamel of the present invention was excellent in adhesion.

Formulation Example 9

Nail Base Coat

| (Ingredient) | (% by mass) |
|---|---|
| 1. Nitrocellulose | 15 |
| 2. Dextrin fatty acid ester of the present invention (Production Example 10) | 0.5 |
| 3. Ethyl acetate | 20 |
| 4. Butyl acetate | balance |
| 5. Heptane | 5 |
| 6. Ethanol | 3 |
| 7. Dibutyl phthalate | 1 |
| 8. Titanium oxide | 0.5 |
| 9. Calcium carbonate | 0.1 |

[Production Method]
A: Ingredients 1 to 2 are added to ingredients 3 to 7 and dissolved using Disper.
B: Ingredients 8 to 9 were further uniformly added and mixed thereinto, and the resulting mixture was charged into a container to obtain a nail base coat.

The obtained nail base coat of the present invention was excellent in adhesion.

Formulation Example 10

Eye Color

| (Ingredient) | (% by mass) |
|---|---|
| 1. Talc | 12 |
| 2. Synthetic Fluorphlogopite | 50 |
| 3. Sericite | balance |
| 4. Titanated mica | 15 |
| 5. Red No. 226 | 0.05 |
| 6. Red No. 202 | 0.1 |
| 7. Ultramarine blue | 1 |
| 8. Titanium oxide | 2 |
| 9. red iron oxide (Colcothar) | 0.2 |
| 10. Yellow iron oxide | 1 |
| 11. Black iron oxide | 0.1 |
| 12. Cetyl 2-ethylhexanoate | 3 |
| 13. Dextrin fatty acid ester of the present invention (Production Example 11) | 0.5 |
| 14. Heavy liquid isoparaffin | 2 |
| 15. Squalane | 5 |
| 16. Antiseptic (methyl parahydroxybenzoate) | 0.3 |

[Production Method]
A: Ingredients 1 to 11 are dispersed by mixing, and dissolved ingredients 12 to 16 are added and mixed thereinto, followed by pulverization.
B: The powder was pressed into a metal case to obtain an eye color.

The obtained eye color of the present invention offered smooth texture and was excellently fitted to the skin.

Formulation Example 11

Crayon

| (Ingredient) | (% by mass) |
|---|---|
| 1. Carnauba wax | 12 |
| 2. Paraffin wax | 12 |
| 3. Beeswax | 4 |
| 4. Dextrin fatty acid ester of the present invention (Production Example 12) | 4 |
| 5. Liquid paraffin | 24 |
| 6. Titanium oxide | 20 |
| 7. Calcium carbonate | 24 |

[Production Method]
A: Ingredients 1 to 5 were dissolved by heating.
B: Ingredients 6 to 7 were dispersed in the solution of A by mixing, and the mixture was then poured into a mold, left at room temperature, and then taken out of the mold to obtain a crayon.

The obtained crayon offered smooth texture and was excellent in adhesion.

Formulation Example 12

Oil White Paint for Metal

| (Ingredient) | (% by mass) |
|---|---|
| 1. Dextrin fatty acid ester of the present invention (Production Example 1) | 1.5 |
| 2. Titanium white (*20) | 60 |
| 3. Dehydrated castor oil-modified alkyd resin varnish | 33 |
| 4. Liquid paraffin | 5 |
| 5. Manganese dryer (*21) | 0.5 |

(*20): MT500B (manufactured by TAYCA)
(*21): JIS K 8997.64 (manufactured by Nihon Kagaku Sangyo Co., Ltd.)

[Production Method]

Ingredients 1 and 4 were dissolved by heating at 80° C. After addition of ingredients 2, 3, and 5 in this order, the mixture was well kneaded at room temperature to prepare oil white paint for metal.

The oil white paint for metal is excellent in dispersion stability and also offers viscosity suitable for painting procedures because its viscosity can be largely reduced by the addition of turpentine oil or a solvent in small amounts and subsequent stirring in use. This paint was easily spreadable and was able to produce a thick coating without leaving brush marks in brush painting. In addition, it had excellent viscosity as paint in such a way that the paint hardly run.

Industrial Applicability

Dextrin fatty acid ester of the present invention has tackiness that has not previously been achieved, is superior in adhesion to the skin, and forms a film without causing gelation of liquid oil. The dextrin fatty acid ester of the present invention further has excellent solubility in an oil solution and transparency and moderate hardness and as such, produces the effect of improving the durability of cosmetics without loads when contained therein. The dextrin fatty acid ester of the present invention further maintains the dispersibility of color materials even in the resulting ink, paint, and stationery.

The invention claimed is:

1. A dextrin fatty acid ester prepared by esterification between dextrin and fatty acids, wherein the dextrin has an average degree of glucose polymerization of 3 to 150; the fatty acids comprise more than 50 mol % and 95 mol % or less, based on the total amount of the fatty acids, of one or more saturated branched fatty acids having 4 to 26 carbon atoms, and 5 mol % or more and less than 50 mol %, based on the total amount of the fatty acids, of one or more fatty acids selected from the group consisting of a saturated linear fatty acid having 2 to 22 carbon atoms, an unsaturated linear or branched fatty acid having 6 to 30 carbon atoms, and a saturated or unsaturated cyclic fatty acid having 6 to 30 carbon atoms;

the degree of substitution by the fatty acids is 1.0 to 3.0 per glucose unit;

the dextrin fatty acid ester is not capable of causing gelation of liquid paraffin having a kinematic viscosity at 40° C. of 8 $mm^2$/s as measured by ASTM D445 test method; and a maximum stress value applied to the point of contact is 30 to 1000 g when a 100 g load is applied to a film using a texture analyzer, kept for 10 seconds, and then separated therefrom at a rate of 0.5 mm/second, wherein the film has been obtained by applying a light liquid isoparaffin solution containing 40% by mass of the dextrin fatty acid ester at a thickness of 400 μm on a glass plate using an applicator, followed by drying.

2. The dextrin fatty acid ester according to claim 1, wherein the saturated branched fatty acid is one or more saturated branched fatty acids having 12 to 22 carbon atoms.

3. A base for a cosmetic, a pharmaceutical drug, a quasi-drug, stationery, paint, or ink, containing the dextrin fatty acid ester according to claim 1.

4. A base for a cosmetic, a pharmaceutical drug, a quasi-drug, stationery, paint, or ink, containing the dextrin fatty acid ester according to claim 2.

* * * * *